United States Patent [19]
Lang et al.

[11] Patent Number: 4,910,341
[45] Date of Patent: Mar. 20, 1990

[54] PROCESS FOR PREPARING N,N'-DISUBSTITUTED NITRO-PARA-PHENYLENEDIAMINES, N,N'-DISUBSTITUTED NITRO-PARA-PHENYLENEDIAMINES, AND INTERMEDIATE OXAZOLIDONES

[75] Inventors: Gerard Lang, Saint-Gratien; Alex Junino, Livry-Gargan, both of France

[73] Assignee: L'Oreal, Paris, France

[21] Appl. No.: 240,619

[22] Filed: Sep. 6, 1988

Related U.S. Application Data

[63] Continuation of Ser. No. 784,948, Oct. 7, 1984, abandoned.

[30] Foreign Application Priority Data

Oct. 9, 1984 [FR] France .................. 84 15498

[51] Int. Cl.$^4$ .................. C09B 51/00
[52] U.S. Cl. .................. 564/413; 8/415; 548/229; 564/367; 564/369; 564/406; 564/441
[58] Field of Search .......... 564/413, 406, 441, 367, 564/369

[56] References Cited

U.S. PATENT DOCUMENTS

| | | | |
|---|---|---|---|
| 3,617,164 | 11/1971 | Kalopissis et al. | 564/441 |
| 3,646,216 | 2/1972 | Cinnamon et al. | 564/367 |
| 3,944,612 | 3/1976 | Bil | 564/441 |
| 4,065,255 | 12/1977 | Andrillon et al. | 8/412 |
| 4,470,826 | 9/1984 | Bugaut et al. | 564/367 |
| 4,727,192 | 2/1988 | Junino et al. | 564/369 |
| 4,736,067 | 4/1988 | Bugaut et al. | 564/441 |
| 4,797,129 | 1/1989 | Junino et al. | 564/441 |
| 4,835,314 | 5/1989 | Konrad | 564/441 |

FOREIGN PATENT DOCUMENTS

| | | |
|---|---|---|
| 1051605 | 9/1953 | France . |
| 1310072 | 10/1962 | France . |
| 85850 | 9/1965 | France . |
| 1565261 | 3/1969 | France . |
| 1575821 | 6/1969 | France . |
| 1581135 | 8/1969 | France . |
| 1150445 | 4/1969 | United Kingdom . |

Primary Examiner—Donald G. Daus
Attorney, Agent, or Firm—Cushman, Darby & Cushman

[57] ABSTRACT

The present invention relates to a process for preparing a N,N'-disubstituted nitro-para-phenylenediamine (I) according to the following scheme:

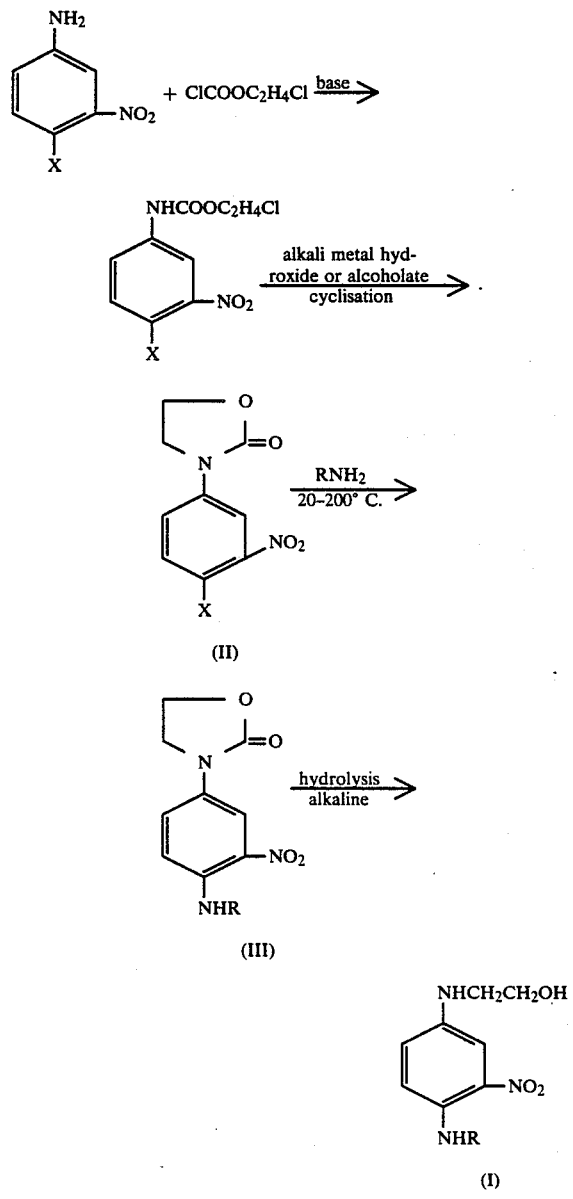

X denoting a halogen and R a lower alkyl, lower mono- or polyhydroxyalkyl, lower alkoxyalkyl or lower aminoalkyl group, in which the amino group can be mono- or disubstituted with a lower alkyl or lower mono- or polyhydroxyalkyl group, the nitrogen atom of said amino group being able to form part of a heterocyclic system.

The invention also relates to the intermediate oxazolidones of formulae (II) and (III), and the new nitro-para-phenylenediamines in which R denotes a lower alkoxyalkyl, lower polyhydroxyalkyl or lower aminoalkyl group, as well as the dyeing compositions for keratinous fibres containing these new nitro-para-phenylenediamines.

5 Claims, No Drawings

PROCESS FOR PREPARING N,N'-DISUBSTITUTED NITRO-PARA-PHENYLENEDIAMINES, N,N'-DISUBSTITUTED NITRO-PARA-PHENYLENEDIAMINES, AND INTERMEDIATE OXAZOLIDONES

This is a continuation of application Ser. No. 06/784,948, filed October 7, 1984 now abandoned.

The present invention relates to a new process for preparing N,N'-disubstituted nitro-para-phenylenediamines, the new oxazolidones used as intermediate compounds in this process, the new N,N'-disubstituted nitro-para-phenylenediamines obtained according to this process and the use of the N,N'-disubstituted nitro-para-phenylenediamines obtained by the said process in dyeing keratinous fibres, and especially human hair.

It is well known that to endow hair with a direct coloration, or with additional glints in the case of oxidation dyeing, it is possible to use nitrated derivatives of the benzene series, and in particular derivatives of nitro-para-phenylenediamine mono-, di- or tri-substituted on the amino groups.

There are already a number of processes by which compounds of this type may be prepared.

For example, French Pat. No. 1,051,605 describes the preparation of N,N'-disubstituted nitro-para-phenylenediamines by reacting glycol chlorohydrin with nitro-para-phenylenediamine. This process leads, in general, to a mixture of compounds corresponding to the mono-, di- and tri-substituted derivatives of nitro-para-phenylenediamine. This mixture contains, in addition, nitro-para-phenylenediamine, and the different derivatives are difficult to separate from the reaction medium.

French Pat. No. 1,310,072 describes a multi-stage process for preparing N,N'-disubstituted nitro-para-phenylenediamines, consisting first in tosylating a 1-alkylamino-2-nitro-4-aminobenzene, then reacting the product with glycol chlorohydrin or glycerol chlorohydrin, and finally hydrolyzing the 1-alkylamino-2-nitro-4[(hydroxyalkyl) (p-toluenesulphonyl)amino]benzene with sulphuric acid to obtain the 1-alkylamino-2-nitro-4-(hydroxyalkylamino)benzene. This process, which is lengthy and expensive, leads to products of moderate purity.

French Pat. No. 1,581,135 describes the preparation of N-substituted or N,N,N'-trisubstituted nitro-para-phenylenediamines by replacement of the fluorine in 4-fluoro-3-nitroaniline or 4-fluoro-3-nitro-N,N-bis(β-hydroxyethyl)aniline using a primary or secondary amine. The preparation of N,N'-disubstituted nitro-para-phenylenediamines is not illustrated in that patent, since the preparation of these compounds is more complicated and requires several stages.

In effect, as is described in French Pat. Nos. 1,565,261 and 1,575,821, it is first necessary to tosylate the 4-fluoro-3-nitroaniline to obtain 4-fluoro-3nitro-N-tosylaniline. This compound is then alkylated with glycol chlorohydrin, the fluorine atom is then replaced by a primary amine, and the product is finally hydrolyzed in sulphuric acid medium to obtain an N,N'-disubstituted nitro-para-phenylenediamine. Nevertheless, this process is lengthy and expensive, and also leads to products of moderate purity.

The Applicants consequently sought a process for preparing N,N'-disubstituted nitro-para-phenylenediamines which was simple and rapid to perform and which enabled products of very high purity to be obtained.

Thus, the Applicants discovered, and this constitutes one of the subjects of the present invention, a process for preparing N,N'-disubstituted nitro-para-phenylenediamines of formula:

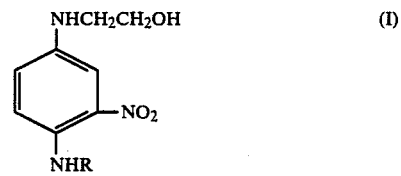

in which R denotes a lower alkyl, lower mono- or polyhydroxyalkyl, lower alkoxyalkyl or lower aminoalkyl radical in which the amino group can be mono- or disubstituted with a lower alkyl or lower mono- or polyhydroxyalkyl radical, the nitrogen atom of said amino group also being able to form a part of a heterocylic system, the process consisting:

(1) in a first stage, in reacting β-chloroethyl chloroformate with a starting 4-halo-3-nitroaniline of formula:

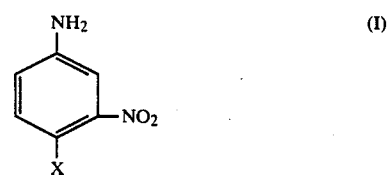

in which X denotes a halogen such as chlorine or fluorine, in a polar organic solvent, preferably dioxane, and in the presence of an inorganic or organic base which traps acids, to obtain the compound of formula:

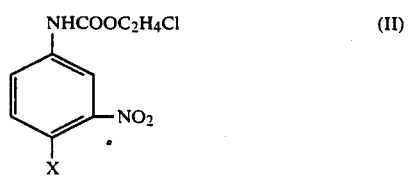

in which X has the same meaning as above, which is cyclized in an organic solvent such as a $C_1$–$C_4$ lower alcohol, in the presence of an alkali metal hydroxide or alcoholate, to obtain an N-(4-halo-3-nitrophenyl)oxazolidone of formula:

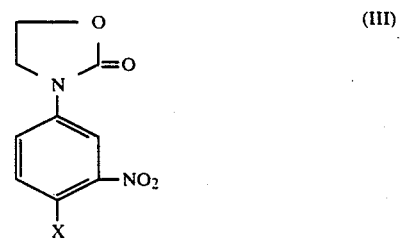

in which X has the meaning indicated above;

(2) in a second stage, in condensing with the oxazolidone of formula (II) a primary amine $RNH_2$ in which R has the meanings indicated above, at a temperature between 20° and 200° C., and preferably between 25° C. and 100° C., optionally in the presence of solvents such as water or C₁–C₄ lower alcohols, to obtain the compound of formula:

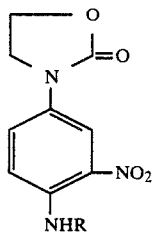

in which R has the meaning indicated above, and (3) in a third stage, in performing alkaline hydrolysis of the compound of formula (III) above, optionally in the presence of an organic solvent such as a C₁–C₄ lower alcohol, to obtain the compound of formula (I), which is optionally isolated in the form of one of its cosmetically acceptable salts.

The present invention also relates to the intermediate oxazolidones of formula:

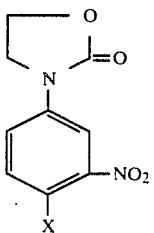

in which X denotes a halogen such as chlorine or fluorine, as well as the oxazolidones of formula:

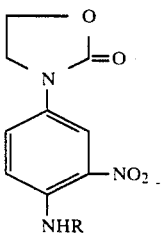

in which R denotes a lower alkyl, lower mono- or polyhydroxyalkyl, lower alkoxyalkyl or lower aminoalkyl radical, in which the amino group can be mono- or disubstituted with a lower alkyl or lower mono- or polyhydroxyalkyl radical, the nitrogen atom of said amino group also being able to form part of a heterocyclic system.

Another subject of the present invention is the new N,N'-disubstituted nitro-para-phenylenediamines of formula:

in which R' denotes a lower alkoxy, lower polyhydroxyalkyl or lower aminoalkyl radical, as well as the cosmetically acceptable salts of these compounds.

A further subject of the present invention consists of a dyeing composition for keratinous fibres, and in particular for human hair, containing a sufficient amount of at least one N,N'-disubstituted nitro-para-phenylendiamine of formula (I') above, or one of its cosmetically acceptable salts, in a solvent medium.

By lower alkyl or lower alkoxy radical, there is understood, according to the present invention, an alkyl or alkoxy radical containing 1 to 6 carbon atoms, and preferably 1 to 4 carbon atoms.

As starting compound in the preparation process of the invention, 4-fluoro-3-nitroaniline or 4-chloro-3-nitroaniline can be used without discrimination. However, it is preferable to use 4-fluoro-3-nitroaniline, which leads to a better yield.

Especially preferred R radicals according to the invention in the compounds of formula (I) are methyl, ethyl, β-hydroxyethyl, γ-hydroxypropyl, β, γ-dihydroxypropyl, methoxyethyl, aminoethyl and β-diethylaminoethyl radicals.

Especially preferred R' radicals according to the invention in the compounds of formula (I') are methoxyethyl, β, γ-dihydroxypropyl and aminoethyl radicals.

The dyeing compositions according to the invention contain at least one compound corresponding to the formula (I'), or one of its cosmetically acceptable salts, in a solvent medium, and can be used for the direct dyeing of keratinous fibres or for the oxidation dyeing of these fibres, in which case compounds of formula (I') confer glints which are complementary to the basic coloration obtained by oxidative development of oxidation dye precursors.

These compositions contain the compounds according to the invention in proportions of between 0.001 and 5% by weight, and preferably between 0.05 and 2% by weight, relative to the total weight of the composition.

The solvent medium is preferably a cosmetic vehicle generally consisting of water, but organic solvents can also be added to the compositions to solubilize compounds which would not be sufficiently soluble in water. Among these solvents, there may be mentioned lower alkanols such as ethanol and isopropanol, aromatic alcohols such as benzyl alcohol, polyols such as glycerol, glycols or glycol ethers such as 2-butoxyethanol or 2-ethoxyethanol, ethylene glycol, propylene glycol, and diethylene glycol monomethyl ether and monoethyl ether, as well as similar products and mixtures thereof. These solvents are preferably present in proportions ranging from 1 to 75% by weight, and especially from 5 to 50% by weight, relative to the total weight of the composition.

These compositions can contain anionic, cationic, nonionic or amphoteric surfactants, or mixtures thereof. These surfactant products are present in the compositions of the invention in proportions of between 0.5 and 55% by weight, preferably between 4 and 40% by weight, relative to the total weight of the composition.

The compositions can be thickened, preferably with compounds chosen from sodium alginate, gum arabic, cellulose derivatives such as methylcellulose, hydroxyethylcellulose, hydroxypropylmethylcellulose and carboxymethylcellulose, and the various polymers having the function of thickener such as, more especially, acrylic acid derivatives. It is also possible to use inorganic thickening agents such as bentonite. These thickening agents are preferably present in proportions of between 0.5 and 10% by weight, and especially between 0.5 and 2% by weight, relative to the total weight of the composition.

The compositions according to the invention can also contain various adjuvants commonly used in dyeing compositions for the hair, and especially penetrating agents, dispersing agents, sequestering agents, film-forming agents, buffers and perfumes.

These compositions can take various forms, such as a liquid, cream, gel or any other form suitable for carrying out hair dyeing. They can, in addition, be packaged in aerosol cans in the presence of a propellant.

The pH of these dyeing compositions can be between 3 and 11.5, and preferably between 5 and 11.5. The pH is adjusted to the desired value by means of an alkalinizing agent such as ammonia solution, sodium carbonate, potassium carbonate or ammonium carbonate, sodium hydroxide or potassium hydroxide, alkanolamines such as mono-, di- or triethanolamine, 2-amino-2-methyl-1-propanol, 2-amino-2-methyl-1,3-propanediol or alkylamines such as ethylamine or triethylamine, or by means of an acidifying agent such as phosphoric, hydrochloric, tartaric, acetic, lactic or citric acid.

When the compounds are intended to be used in a process for direct dyeing of hair, they can contain, in addition to the compounds according to the invention, other direct dyes such as azo or anthraquinone dyes, such as, for example, 1,4,5,8-tetraaminoanthraquinone, or nitrated dyes of the benzene series other than the compounds of formula (I').

The concentrations of these direct dyes other than the dyes of formula (I') can be between 0.001 and 5% by weight relative to the total weight of the composition.

These compositions, employed in a process for dyeing by direct dyeing, are applied on the keratinous fibres for an exposure time varying from 5 to 50 minutes, and the fibres are then rinsed, optionally washed, rinsed again and dried.

The compounds according to the invention can also be employed in the form of hairsetting lotions, intended both to endow the hair with a slight coloration or glints and to improve the shape-retention of the setting. In this case, they take the form of aqueous, alcoholic or hydroalcoholic solutions containing at least one cosmetic resin, and they are applied on damp hair, washed and rinsed beforehand, which is optionally rolled up and then dried.

The cosmetic resins used in the setting lotions can be, in particular, polyvinylpyrrolidone, crotonic acid/vinyl acetate, vinylpyrrolidone/vinyl acetate, maleic anhydride/butyl vinyl ether, or maleic anhydride/methyl vinyl ether copolymers, or any other cationic, anionic, nonionic or amphoteric polymer commonly used in this type of composition. These cosmetic resins are incorporated in the compositions of the invention in the proportion of 0.5 to 4% by weight, and preferably from 1 to 3% by weight, based on the total weight of the composition.

When the compositions according to the invention constitute oxidation dyeing compositions, involving development with an oxidizing agent, the compounds of formula (I') according to the invention are mainly used for the purpose of contributing glints to the final dyeing effect.

These compositions then contain oxidation dye precursors in combination with at least one nitrated dye of formula (I') and optionally other direct dyes.

They can contain, for example, para-phenylenediamines such as para-phenylenediamine, paratoluylenediamine, 2-chloro-para-phenylenediamine, 2,6-dimethyl-para-phenylenediamine, 2,6-dimethyl-3-methoxy-para-phenylenediamine, N-($\beta$-methoxyethyl)-para-phenylenediamine, N,N-bis($\beta$-hydroxyethyl)-para-phenylenediamine and 4-[ethyl-(carbamylmethyl)amino]aniline, as well as the salts thereof.

They can also contain para-aminophenols, for example para-aminophenol, N-methyl-para-aminophenol, 2-chloro-4-aminophenol, 3-chloro-4-aminophenol and 2-methyl-4-aminophenol, and the salts thereof.

They can also contain ortho-aminophenol.

They can, in addition, contain heterocyclic derivatives, for example 2,5-diaminopyridine and 7-aminobenzomorpholine.

Compositions according to the invention can contain, in combination with the oxidation dye precursors, couplers which are well known in the state of the art.

By way of couplers, meta-diphenols, meta-aminophenols and the salts thereof, meta-phenylenediamines and the salts thereof, meta-(acylamino)phenols, meta-ureido-phenols and meta-(carbalkoxyamino)phenols may be mentioned in particular.

As other couplers which can be used in the compositions of the invention, $\alpha$-naphthol, couplers possessing an active methylene group such as diketo compounds and pyrazolones and heterocyclic couplers derived from pyridine and benzomorpholine may finally be mentioned.

These compositions contain, in addition to the oxidation dye precursors, reducing agents present in proportions of between 0.05 and 3% by weight relative to the total weight of the composition.

The oxidation dye precursors can be used, in the compositions of the invention, at concentrations of between 0.001 and 5% by weight, and preferably between 0.03 and 2% by weight, based on the total weight of the composition. The couplers can also be present in proportions of between 0.001 and 5% by weight, and preferably between 0.015 and 2% by weight. The pH of these oxidation dyeing compositions is preferably between 7 and 11.5, and is adjusted by means of alkalinizing agents defined above.

The process for dyeing keratinous fibres, in particular human hair, employing development with an oxidizing agent, consists in applying on the hair the dyeing composition comprising both a dye according to the invention and the dye precursors. The development of the coloration can then be accomplished slowly in the presence of the oxygen in the air, but a chemical development system is preferably used, and this is most frequently chosen from hydrogen peroxide, urea peroxide and persalts. In particular, "20 volumes" hydrogen peroxide solution is used.

When the composition with the oxidizing agent has been applied on the keratinous fibres, it is left in place for 10 to 50 minutes, preferably 15 to 30 minutes, after which the keratinous fibres are rinsed, optionally washed with a shampoo, rinsed again and dried.

The examples which follow are intended to illustrate the invention without being limitative in nature.

EXAMPLE No. 1

Preparation of N-(4-fluoro-3-nitrophenyl)oxazolidone

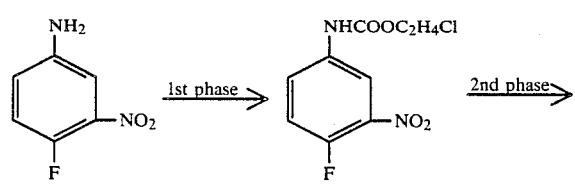

1st phase: Condensation of β-chloroethyl chloroformate with 4-fluoro-3-nitroaniline A mixture consisting of 0.4 mole (62.4 g) of 4-fluoro-3-nitroaniline and 0.22 mole (22 g) of calcium carbonate in 190 ml of dioxane is heated to 90° C.

0.44 mole (45.5 ml) of β-chloroethyl chloroformate is allowed to run in.

The mixture is stirred for 10 minutes at 100° C. after the addition is complete.

20 ml of water are added to the reaction medium; the solution is filtered in order to remove a resin. The filtrate is poured into 500 ml of iced water. After the precipitate obtained has been filtered off, washed with water and dried under vacuum, 133 g of the expected product, which crystallizes with 1 molecule of dioxane, are obtained.

After recrystallization from benzene, it melts at 74° C.

Analysis gives the following results:

| Analysis | Calculated for $C_9H_8N_2O_4FCl$ | Found |
|---|---|---|
| C | 41.14 | 40.92 |
| H | 3.05 | 3.10 |
| N | 10.66 | 10.71 |
| Cl | 13.52 | 13.31 |

2nd phase: Preparation of N-(4-fluoro-3-nitrophenyl)-oxazolidone

The product obtained in phase 1 is suspended in 400 ml of ethanol, and 0.4 mole (72 g) of a 30% strength solution of sodium methylate in methanol is added in a single portion. After 5 minutes' stirring, the temperature of the reaction medium reaches 46° C. and the formation of a precipitate is observed. After an additional 10 minutes' stirring, the precipitate is drained, washed with ethanol, then with water and with ethanol. After being dried under vacuum, 77 g of the expected product are obtained. It melts at 135° C.

Analysis gives the following results:

| Analysis | Calculated for $C_9H_7N_2O_4F$ | Found |
|---|---|---|
| C | 47.79 | 47.61 |
| H | 3.10 | 3.19 |
| N | 12.39 | 12.41 |

EXAMPLE No. 2

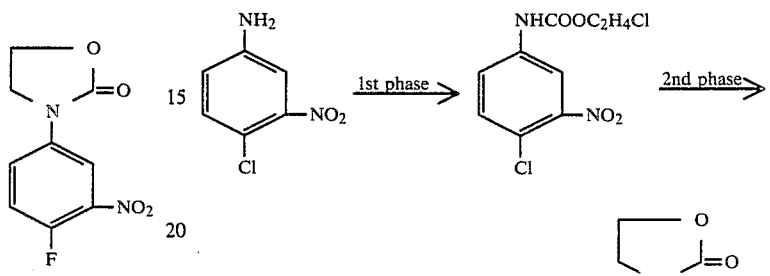

1st phase: Condensation of β-chloroethyl chloroformate with 4-chloro-3-nitroaniline The procedure is identical to that used in Example 1 (first phase).

The treatment of 0.6 mole (103.5 g) of 4-chloro-3-nitroaniline leads, after recrystallisation from a dimethylformamide/water mixture, to 0.57 mole (160 g) of the expected product. It melts at 114° C.

Analysis gives the following results:

| Analysis | Calculated for $C_9H_8N_2O_4Cl_2$ | Found |
|---|---|---|
| C | 38.73 | 38.70 |
| H | 2.89 | 2.96 |
| N | 10.04 | 9.95 |
| O | 22.93 | 23.02 |
| Cl | 25.41 | 25.57 |

2nd phase: Preparation of N-(4-chloro-3-nitrophenyl)oxazolidone 0.56 mole (159.1 g) of the product prepared in the first phase is introduced into 650 ml of 96° strength ethanol. With the temperature maintained at 20° C.–25° C., a solution of sodium hydroxide in water, prepared by dissolving 0.69 mole (27.6 g) of sodium hydroxide pellets in 170 ml of water, is added dropwise.

Stirring is continued for half an hour after the addition is complete. After the reaction medium has been cooled, the precipitate is drained. After this has been made into a paste in water at neutrality, followed by washing with isopropanol and drying at 55° C. under vacuum, a product is obtained which, after recrystallization from a dimethylformamide/water mixture melts at 160° C.

Analysis gives the following results:

| Analysis | Calculated for C₉H₇N₂O₄Cl | Found |
|---|---|---|
| C | 44.55 | 44.44 |
| H | 2.90 | 3.00 |
| N | 11.60 | 11.72 |
| O | 26.38 | 26.20 |
| Cl | 14.61 | 14.84 |

EXAMPLE No. 3

Preparation of N-(4-methylamino-3-nitrophenyl)oxazolidone

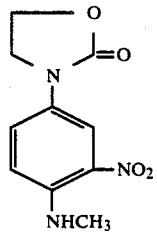

0.05 mole (11.3 g) of N-(4-fluoro-3-nitrophenyl)oxazolidone, prepared according to Example 1, is introduced into 45 ml of a 33% strength solution of methylamine in alcohol. After being stirred for 2 h 30 min at 20° C. the reaction mixture is poured into water. The precipitate is drained, washed with water and alcohol, and then dried under vacuum. 0.049 mole (11.85 g) of the expected product is obtained. It melts at 192° C.

Analysis gives the following results:

| Analysis | Calculated for C₁₀H₁₁N₃O₄ | Found |
|---|---|---|
| C | 50.63 | 50.41 |
| H | 4.64 | 4.69 |
| N | 17.72 | 17.64 |
| O | 27.00 | 26.86 |

EXAMPLE No. 4

Preparation of N-(4-ethylamino-3-nitrophenyl)oxazolidone

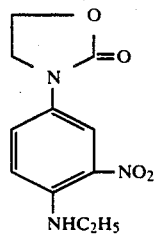

0.05 mole (11.3 g) of N-(4-fluoro-3-nitrophenyl)oxazolidone, prepared according to Example 1, is introduced into 45 ml of a 33% strength solution of ethylamine in water. The suspension is heated for 1 hour at 95° C. The formation of a precipitate is observed, and this is drained after the reaction medium has been poured into an ice/water mixture. After being washed in ethanol and dried, the product obtained melts at 140° C.

Analysis gives the following results:

| Analysis | Calculated for C₁₁H₁₃N₃O₄ | Found |
|---|---|---|
| C | 52.59 | 52.48 |
| H | 5.18 | 5.20 |
| N | 16.73 | 16.70 |
| O | 25.50 | 25.80 |

EXAMPLE No. 5

Preparation of N-[4-(β-hydroxyethyl)amino-3-nitrophenyl]oxazolidone

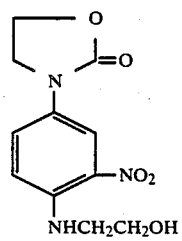

0.31 mole (70 g) of N-(4-fluoro-3-nitrophenyl)oxazolidone is introduced into 280 ml of monoethanolamine; the mixture is brought to a boiling water bath; a precipitate appears rapidly. The reaction medium is poured into 600 ml of iced water.

After the precipitate has been drained, washed with water, and then dried under vacuum, 0.29 mole (77.5 g) of the expected product is obtained. It melts at 184° C.

Analysis gives the following results:

| Analysis | Calculated for C₁₁H₁₃N₃O₅ | Found |
|---|---|---|
| C | 49.44 | 49.37 |
| H | 4.87 | 4.79 |
| N | 15.73 | 15.82 |
| O | 29.96 | 29.92 |

EXAMPLE No. 6

Preparation of N-[4-(γ-hydroxypropyl)amino-3-nitrophenyl]oxazolidone

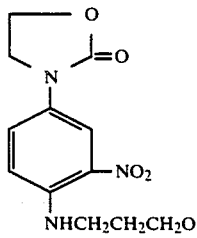

0.02 mole (4.5 g) of N-(4-fluoro-3-nitrophenyl)oxazolidone is introduced into 10 ml of 3-amino-1-propanol.

After 1 hour's heating at 95° C., the mixture is poured into 100 ml of iced water acidified with hydrochloric acid.

The orange-colored precipitate thereby obtained is drained, and made into a paste in water. It melts at 159° C.

Analysis gives the following results:

| Analysis | Calculated for $C_{12}H_{13}N_3O_5$ | Found |
|---|---|---|
| C | 51.24 | 51.13 |
| H | 5.38 | 5.41 |
| N | 14.94 | 14.97 |
| O | 28.44 | 28.20 |

EXAMPLE No. 7

Preparation of N-[4-($\beta$-methoxyethyl)amino-3-nitrophenyl]oxazolidone

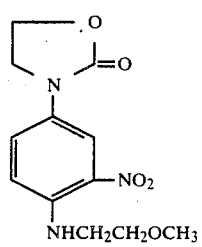

NHCH₂CH₂OCH₃

0.025 mole (5.65 g) of the fluorinated oxazolidone prepared according to Example 1 is added to 23 ml of methoxyethylamine. The reaction mixture is brought to 95° C. After being stirred for 10 minutes, the mixture is poured onto ice. The precipitate obtained is drained, and washed with water and then alcohol. After recrystallization from alcohol and drying under vacuum, it melts at 148° C.

Analysis gives the following results:

| Analysis | Calculated for $C_{12}H_{15}N_3O_5$ | Found |
|---|---|---|
| C | 51.24 | 51.21 |
| H | 5.34 | 5.31 |
| N | 14.95 | 15.12 |
| O | 28.47 | 28.25 |

EXAMPLE No. 8

Preparation of N-[4-($\gamma$-hydroxypropyl)amino-3-nitrophenyl]oxazolidone 0.2 mole (48.5 g) of the chlorinated oxazolidone prepared according to Example 2 is added to 100 ml of 3-amino-1-propanol. The mixture is heated for 2 h 30 min at 95° C. The reaction medium is poured onto 100 g of ice to which 8 ml of concentrated hydrochloric acid have been added.

After being drained, washed and dried, the precipitate obtained (0.053 mole; 14.8 g) melts at 159° C. It is identical to the product obtained in Example 6.

EXAMPLE No. 9

Preparation of N-[4-($\beta,\gamma$-dihydroxypropyl)amino-3-nitrophenyl]oxazolidone

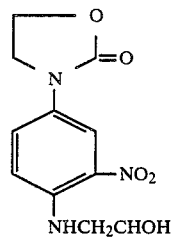

NHCH₂CHOHCH₂OH 0.05 mole (11.3 g) of the fluorinated oxazolidone prepared according to Example 1 is introduced into 45 ml of a solution of 3-amino-1,2-propanediol. After being heated for 1 h 30 min at 95° C., the solution is poured onto ice. The precipitate is drained, washed and dried under vacuum. 0.048 mole (14.2 g) of an orange-red product is obtained. After recrystallization from ethanol, it melts at 150° C.

Analysis gives the following results:

| Analysis | Calculated for $C_{12}H_{15}N_3O_6$ | Found |
|---|---|---|
| C | 48.48 | 48.45 |
| H | 5.05 | 5.15 |
| N | 14.14 | 14.25 |
| O | 32.32 | 32.15 |

EXAMPLE No. 10

Preparation of N-[4-($\beta$-aminoethyl)amino-3-nitrophenyl]oxazolidone

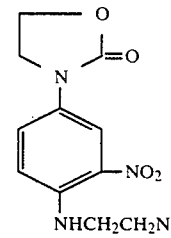

NHCH₂CH₂NH₂

To 45 ml of pure ethylenediamine, 0.05 mole (11.3 g) of N-(4-fluoro-3-nitrophenyl)oxazolidone is added in the cold with stirring.

The temperature reaches 75° C. The reaction medium is poured onto ice. The precipitate is drained, and washed with water and ethanol. After recrystallization, it melts at 162° C.

Analysis gives the following results:

| Analysis | Calculated for $C_{11}H_{14}N_4O_4$ | Found |
|---|---|---|
| C | 49.62 | 49.53 |
| H | 5.26 | 5.32 |
| N | 21.05 | 21.22 |
| O | 24.06 | 24.25 |

EXAMPLE No. 11

Preparation of
N-{4-[β-(diethylamino)ethyl]amino-3-nitrophenyl}oxazolidone

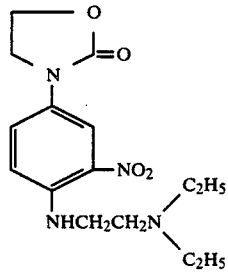

0.05 mole (11.3 g) of the fluorinated oxazolidone prepared according to Example 1 is added to 45 ml of 2-(diethylamino)ethylamine. After being stirred for 1 h 30 min at room temperature, the reaction medium is poured onto ice. The precipitate formed is drained, and washed with water and then ethanol. After being dried under vacuum, 0.049 mole (16 g) of a product melting at 124° C. is obtained.

Analysis gives the following results:

| Analysis | Calculated for $C_{15}H_{22}N_4O_4$ | Found |
|---|---|---|
| C | 55.90 | 56.02 |
| H | 6.83 | 6.87 |
| N | 17.39 | 17.59 |
| O | 19.88 | 20.04 |

EXAMPLE No. 12

Preparation of
1-methylamino-2-nitro-4-[(β-hydroxyethyl)amino]benzene

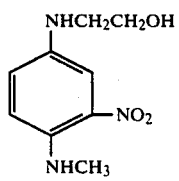

0.04 mole (9.5 g) of N-(4-methylamino-3-nitrophenyl)oxazolidone, prepared according to Example 3, is introduced into a solution of 27 ml of 3N sodium hydroxide and 10 ml of ethanol at 95° C. After being heated for 2 hours on a boiling water bath, the solution is poured onto ice. After being drained and washed with water, the precipitate is dried under vacuum.

0.038 mole (8 g) of the expected product is obtained. It melts at 114° C.

EXAMPLE No. 13

Preparation of
1-ethylamino-2-nitro-4-[(β-hydroxyethyl)amino]benzene

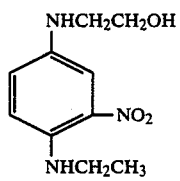

By a treatment identical to that used in Example 12, 0.04 mole (10.04 g) of N-(4-ethylamino-3-nitrophenyl)oxazolidone, prepared according to Example 4, leads to 0.039 mole (8.8 g) of the expected product. It melts at 106° C.

Analysis gives the following results:

| Analysis | Calculated for $C_{10}H_{15}N_3O_3$ | Found |
|---|---|---|
| C | 53.33 | 53.13 |
| H | 6.67 | 6.69 |
| N | 18.67 | 18.81 |
| O | 21.33 | 21.50 |

EXAMPLE No. 14

Preparation of
1-(β-hydroxyethyl)amino-2-nitro-4-[(β-hydroxyethyl)amino]benzene

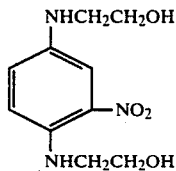

0.2 mole (53.4 g) of N-[4-(β-hydroxyethyl)amino-3-nitrophenyl]oxazolidone, prepared according to Example 5, is treated with 135 ml of 3N sodium hydroxide to which 55 ml of 96° strength ethanol has been added. 0.18 mole (44.2 g) of the expected product is obtained. It melts at 107° C.

EXAMPLE No. 15

Preparation of
1-(γ-hydroxypropyl)amino-2-nitro-4-[(β-hydroxyethyl)amino]benzene

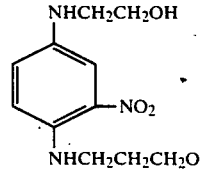

0.02 mole (5.1 g) of N-[4-(γ-hydroxypropyl)amino-3-nitrophenyl]oxazolidone, prepared according to Example 6 or 8, is added to 22 moles of 2N sodium hydroxide. After 30 minutes' heating at 80° C., the expected product crystallizes from the reaction medium.

After being cooled, the precipitate is drained, washed with water and dried under vacuum. 0.016 mole (4 g) of a product melting at 90° C. is obtained.

Analysis gives the following results:

| Analysis | Calculated for $C_{11}H_{17}O_4N_3$ | Found |
|---|---|---|
| C | 51.76 | 51.70 |
| H | 6.66 | 6.74 |
| N | 16.47 | 16.45 |
| O | 25.10 | 25.11 |

EXAMPLE No. 16

Preparation of
1-(β-methoxyethyl)amino-2-nitro-4-[(β-hydroxyethyl)amino]benzene

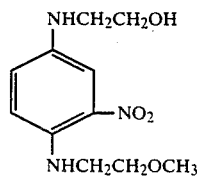

0.02 mole (5.6 g) of N-[4-(β-methoxyethyl)amino-3-nitrophenyl]oxazolidone, prepared according to Example 7, is added to 13.5 ml of 3N sodium hydroxide and 5.6 ml of 96° strength ethanol.

The suspension is heated for 15 minutes at 95° C., and then poured onto ice. The precipitate obtained is drained, washed with iced water and dried under vacuum. After recrystallization from benzene, it melts at 68° C.

Analysis gives the following results:

| Analysis | Calculated for $C_{11}H_{17}N_3O_4$ | Found |
|---|---|---|
| C | 51.76 | 51.58 |
| H | 6.67 | 6.64 |
| N | 16.47 | 16.48 |
| O | 25.10 | 24.89 |

EXAMPLE No. 17

Preparation of
1-(β,γ-dihydroxypropyl)amino-2-nitro-4-[(β-hydroxyethyl)amino]benzene

0.04 mole (11.9 g) of N-[4-(β,γ-dihydroxypropyl)amino-3-nitrophenyl]oxazolidone, prepared according to Example 9, is added to 27 ml of sodium hydroxide to which 12 ml of 96° strength ethanol have been added. After being heated for 45 minutes on a boiling water bath, the reaction medium is poured into water and then extracted with ethyl acetate. A solution of hydrochloric acid in ethanol is added. The hydrochloride formed is drained and then washed with ethyl acetate. By treatment with ammonia solution (22° Bé), a product is obtained which, after recrystallization from ethanol, melts at 102° C.

Analysis gives the following results:

| Analysis | Calculated for $C_{11}H_{17}N_3O_5$ | Found |
|---|---|---|
| C | 48.7 | 48.71 |
| H | 6.27 | 6.26 |
| N | 15.50 | 15.45 |
| O | 29.50 | 29.43 |

EXAMPLE No. 18

Preparation of
1-(β-aminoethyl)amino-2-nitro-4-[(β-hydroxyethyl)amino]benzene

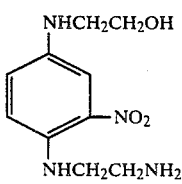

0.4 mole (10.64 g) of N-[4-(β-aminoethyl)amino-3-nitrophenyl]oxazolidone, prepared according to Example 10, is added to 27 ml of 3N sodium hydroxide and 11 ml of 96° strength ethanol. After being heated for 45 minutes at 95° C., the solution is poured onto ice, and the precipitate obtained is drained and then washed with iced water. After being dried under vacuum, 0.036 mole (8.7 g) of the expected product is obtained. It melts at 112° C.

Analysis gives the following results:

| Analysis | Calculated for $C_{10}H_{16}N_4O_3$ | Found |
|---|---|---|
| C | 50.00 | 49.79 |
| H | 6.67 | 6.77 |
| N | 23.33 | 23.56 |
| O | 20.00 | 20.30 |

EXAMPLE No. 19

Preparation of
1-[β-(diethylamino)ethyl]amino-2-nitro-4-[(β-hydroxyethyl)amino]benzene dihydrochloride

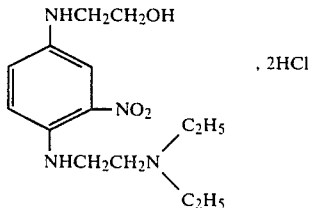

0.04 mole (12.9 g) of N-{4-[β-(diethylamino)ethyl]amino-3-nitrophenyl}oxazolidone, prepared according to Example 11, is added to 27 ml of 3N sodium hydroxide and 13 ml of 96° strength ethanol. After being heated for 45 minutes at 95° C., the reaction medium is poured onto ice.

The expected product is extracted with ethyl acetate.

By addition of ethanol acidified with hydrochloric acid to the ethyl acetate phase, followed by filtration, the product is isolated in the form of the dihydrochloride. 0.037 mole (13.7 g) is obtained.

Molecular mass found by potentiometric assay using sodium hydroxide in water: 369.5.

Molecular mass calculated for $C_{14}H_{26}N_4O_3Cl_2$: 369.5.

Analysis gives the following results:

| Analysis | Calculated for $C_{14}H_{26}N_4O_3Cl_2$ | Found |
|---|---|---|
| C | 45.53 | 45.51 |
| H | 7.05 | 7.11 |
| N | 15.18 | 15.43 |
| O | 13.00 | 13.22 |
| Cl | 19.24 | 19.04 |

APPLICATION EXAMPLE 1

The following dyeing mixture is prepared:

| | |
|---|---|
| 1-(β-Methoxyethyl)amino-2-nitro-4-[(β-hydroxyethyl)amino]benzene (compound of Example 16) | 0.02 g |
| Monoethanolamine, 20% strength by weight | 5 g |
| 2-Butoxyethanol | 10 g |
| CELLOSIZE W.P. 03, UNION CARBIDE (hydroxyethylcellulose) | 2 g |
| Ammonium lauryl sulphate | 5 g |
| Water q.s. | 100 g |
| pH 10.1 | |

This mixture, applied for 20 minutes at 28° C. on bleached hair, endows it, after shampooing and rinsing, with a coloration: 7 YR 6.8/2.5, according to Munsell's notation.

APPLICATION EXAMPLE 2

The following dyeing mixture is prepared:

| | |
|---|---|
| 1-(β,γ-Dihydroxypropyl)amino-2-nitro-4-[(β-hydroxyethyl)amino]benzene (compound of Example 17) | 0.5 g |
| Alcohol, 96° strength | 10 g |
| Triethanolamine | 0.5 g |
| CELLOSIZE W.P. 03, UNION CARBIDE (hydroxyethylcellulose) | 2 g |
| (Tallow alkyl)dimethylhydroxyethylammonium chloride | 2 g |
| Water q.s. | 100 g |
| pH 5 | |

This mixture, applied for 20 minutes at 28° C., on permanently-waved grey hair, endows it, after shampooing and rinsing, with a coloration: 1.8 RP 3.6/3.1 according to Munsell's notation.

APPLICATION EXAMPLE 3

The following dyeing mixture is prepared:

| | |
|---|---|
| 1-(β-Aminoethyl)amino-2-nitro-4-[(β-hydroxyethyl)amino]benzene (compound of Example 18) | 1 g |
| 2-Butoxyethanol | 15 g |
| CARBOPOL 934 (GOODRICH CHEMICALS) (crosslinked polyacrylic acid) | 2 g |
| Water q.s | 100 g |
| pH 9.5 | |

This mixture, applied for 30 minutes at 28° C. on hair naturally 90% white, endows it, after shampooing and rinsing, with a coloration: 3.8 RP 2.9/3.3 according to Munsell's notation.

APPLICATION EXAMPLE 4

The following dyeing mixture is prepared:

| | |
|---|---|
| 1-(β-Methoxyethyl)amino-2-nitro-4-[(β-hydroxyethyl)amino]benzene (compound of Example 16) | 0.5 g |
| Vinyl acetate/crotonic acid copolymer (90% vinyl acetate, 10% crotonic acid; molecular weight 45,000 to 50,000) | 2 g |
| Alcohol, 96° strength | 50 g |
| Ammonia solution, 22° B. q.s. pH 9 | |
| Water q.s. | 100 g |

This composition is applied as a setting lotion on bleached hair. After being dried, the hair shows a pale Parme coloration.

We claim:

1. A process for preparing an N,N'-disubstituted nitro-para-phenylenediamine of the formula

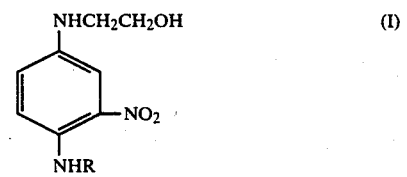

wherein
R represents lower alkyl, lower monohydroxyalkyl, lower polyhydroxyalkyl, lower alkoxyalkyl or lower aminoalkyl wherein the amino group can be mono- or disubstituted with lower alkyl, lower monohydroxyalkyl or lower polyhydroxyalkyl, said process consisting of
(1) in a first stage, reacting β-chloroethyl chloroformate with a 4-halo-3-nitroaniline of the formula

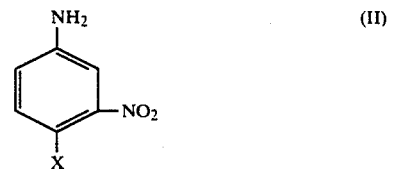

wherein
X represents a halogen selected from the group consisting of chlorine and fluorine, in a polar organic solvent and in the presence of an inorganic or organic base which traps acids, so as to obtain a compound of the formula

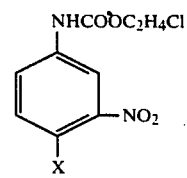

wherein X has the meaning given above, said compound being isolated and then cyclized in an organic solvent in the presence of an alkali metal hydroxide or alkali metal alcoholate so as to obtain an N-(4-halo-3-nitrophenyl) oxazolidone of the formula

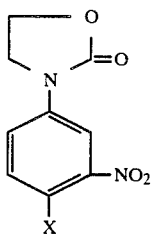

wherein X has the meaning given above, and isolating said oxazolidone;

(2) in a second stage, condensing said isolated oxazolidone of formula (III) with a primary amine of the formula $RNH_2$ wherein R has the meaning given above at a temperature between 20° and 200° C., so as to obtain a compound of the formula:

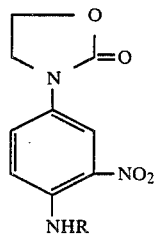

wherein R has the meaning given above, and isolating said compound of formula (IV); and (3) in a third stage, performing alkaline hydrolysis of said isolated compound of formula (IV) in the presence of an organic solvent so as to obtain the compound of formula (I) which is optionally isolated in the form of a cosmetically acceptable salt.

2. The process of claim 1 wherein X is fluorine.

3. The process of claim 1 wherein R represents methyl, ethyl, β-hydroxyethyl, γ-hydroxypropyl, β,γ-dihydroxypropyl, methoxyethyl, aminoethyl or β-diethylaminoethyl.

4. The process of claim 1 wherein said organic solvent in said first and third stages is a $C_1$–$C_4$ lower alcohol.

5. The process of claim 1 wherein water or a $C_1$–$C_4$ lower alcohol is used as a solvent in said second stage.

* * * * *